(12) United States Patent
Clark et al.

(10) Patent No.: US 7,276,261 B2
(45) Date of Patent: Oct. 2, 2007

(54) METHOD FOR PREPARING A ROLLER DRIED PROTEIN PREPARATION

(75) Inventors: David Callam Clark, St. Michielsgestel (NL); Tillmann Gerhard Schmelter, DW Veghel (NL); Johannes Henricus Van Dijk, TN Odiliapeel (NL)

(73) Assignee: Campina B.V. (NL)

( * ) Notice: Subject to any disclaimer, the term of this patent is extended or adjusted under 35 U.S.C. 154(b) by 3 days.

(21) Appl. No.: 10/239,252

(22) PCT Filed: Mar. 22, 2001

(86) PCT No.: PCT/EP01/03436

§ 371 (c)(1),
(2), (4) Date: Dec. 18, 2002

(87) PCT Pub. No.: WO01/70042

PCT Pub. Date: Sep. 27, 2001

(65) Prior Publication Data

US 2003/0104118 A1    Jun. 5, 2003

(30) Foreign Application Priority Data

Mar. 23, 2000 (EP) .................................. 00/02618

(51) Int. Cl.
*A23J 1/20* (2006.01)
(52) U.S. Cl. ................ 426/657; 426/42; 426/471; 426/656
(58) Field of Classification Search ................ 426/656, 426/42, 46, 49, 52, 53, 56, 471, 657
See application file for complete search history.

(56) References Cited

U.S. PATENT DOCUMENTS

| | | | | |
|---|---|---|---|---|
| 3,697,284 A | * | 10/1972 | Miller | ........................ 514/241 |
| 3,711,290 A | * | 1/1973 | Miller | ............................ 426/2 |
| 3,720,765 A | | 3/1973 | Miller | |
| 3,726,972 A | * | 4/1973 | Miller | ......................... 514/21 |
| 3,808,305 A | * | 4/1974 | Gregor | .................. 264/331.12 |
| 4,016,147 A | | 4/1977 | Fujimaki et al. | |
| 4,133,901 A | | 1/1979 | Fetzer et al. | |
| 4,138,505 A | | 2/1979 | Hart et al. | |
| 6,592,927 B1 | * | 7/2003 | Kruger et al. | .............. 426/588 |

FOREIGN PATENT DOCUMENTS

WO     99/51107    * 10/1999

OTHER PUBLICATIONS

Imm, J.Y. et al. "Gelation and water-binding properties of transglutaminase-treated skim milk powder"*Journal of Food Science* 65(2):200-205 (2000).

* cited by examiner

*Primary Examiner*—Anthony Weier
(74) *Attorney, Agent, or Firm*—The Webb Law Firm

(57) ABSTRACT

A method for preparing a dried protein preparation, including roller drying a protein solution having a relatively low protein content of less than 40%, wherein the proteins in the solution are intermolecularly crosslinked by covalent bonds, for example by means of enzymatic treatment, such as with transglutaminase.

6 Claims, 6 Drawing Sheets

METHOD FOR PREPARING A ROLLER DRIED PROTEIN PREPARATION

BACKGROUND OF THE INVENTION

1. Field of the Invention

The present invention relates to a method for preparing a dried protein preparation.

2. Description of the Prior Art

The preparation of protein powders can for example be achieved by means of spray drying. Spray drying can be effected with starting solutions with protein contents in the range 5-20% (w/w). Protein solutions are frequently processed and atomised at these concentrations as their viscosity properties (0.1-0.5 Pa·s (at a shear rate of 100 $s^{-1}$ at 70° C. (Physica UDS200 rheometer, DIN double gap Z1 geometry) mean that they are easily handled and pumped through standard processing equipment. Spray drying of solutions at the lower end of this protein concentration range can result in high levels of dusting (dust formation), which can result in reduced yields and increased risk of dust explosions. An additional disadvantage of spray drying powders can be the poor wettability and dispersibility properties of the dried powders, which have a low density and tend to float on the surface of water-based liquids.

Powders produced by roller drying are characterized by higher densities and improved wetting and dispersing properties. However, these protein powders have a less favourable taste profile, and have a darker colour than their spray dried equivalents. These defects can be ascribed to the high protein concentration (around 40%) needed for an efficient roller drying process.

Lowering the solids or protein concentration in the roller drying process to e.g. 20% (like in spray drying) would solve this problem. However, protein solutions in the 5-20% (w/w) concentration range do not lend themselves to roller drying. They become too fluid when applied to steam heated rollers and spread to form too thin a film, which burns onto the roller. The resulting film cannot be removed efficiently from the roller as a continuous film by the knives used for this purpose, but the protein is rather removed as scorched dust. Alternatively, a double (twin) roller dryer type can be used in which the protein solution subject to drying is contained in a "pool" between the two roller drums. However, the long residence time in this pool at elevated temperatures causes similar defects to the protein (browning) as observed in a high solids single drum dryer process. Additionally, under these conditions the formation of lysinoalanine (LAL) may be favored, which is not desirable.

SUMMARY OF THE INVENTION

It is therefore the object of the present invention to provide a new method of drying proteins, that obviates the above stated drawbacks.

This object is achieved according to the invention by a method comprising roller drying a protein solution having a relatively low protein content of less than 40% (w/w), preferably significantly less than 40% (w/w), wherein the proteins in the solution are crosslinked by covalent bonds. The protein content is preferably 15-25% (w/w), more preferably about 20% (w/w). These protein contents correspond to a viscosity in the range 1-10 Pa·s (double gap, Z1 geometry, shear rate 100 $s^{-1}$ at 70° C.). It was surprisingly found that protein solutions having such relatively low protein content are still viscous enough after crosslinking to be suitable for roller drying. Roller drying is a much simpler technique than spray drying and requires far less complicated equipment. Therefore, malfunction or disturbance of the equipment is less likely to occur than in the case of spray drying.

In addition, no double drum dryer type is needed, since the solution of this cross-linked protein preparation is now viscous enough to be applied on a single drum dryer. This implies that no extra investment for a special drying technique is needed.

The proteins can be crosslinked in various ways. It is however preferred that they are crosslinked by means of enzymatic treatment. A particularly suitable crosslinking enzyme is transglutaminase although others such as peroxidases (such as lactoperoxidase, horse radish peroxidase or myeloperoxidase), laccases or mono amine oxidases are also useful. In addition, proteases can be used as crosslinking enzymes, when their peptidolytic action is reversed, which may be achieved under specified conditions, known as the so-called 'plastein' reaction. The crosslinking is achieved prior to roller drying by exposing an amount of protein to an amount of crosslinking enzyme during an amount of reaction time. For each protein suitable process conditions can be empirically defined. However, as a general rule the amount of protein is 5-30% (w/w), the amount of crosslinking enzyme is 0.01-20 units per gram protein and the reaction time is 0.5-12 hours.

The specific activity of transglutaminase is determined using the method as described by J. E. Folk and P. W. Cole, (1966), J. Biol. Chem., 241, 5518-5525.

The powder resulting from the method as claimed differs from spray dried protein powders in that it is characterized by a higher density, improved wettability and dispersibility. The powder is therefore also part of this invention. A powder of the invention can be characterised by means of its viscosity and microscopic analysis. The viscosity of the product of the invention after redissolving the powder in water at 20% protein varies between 1 and 20 Pa·s. The differences in microscopic appearance between roller dried and spray dried powders can be seen from FIGS. 5 and 6.

The powder of the invention can be used as a waterbinding agent, emulsifying agent, viscosity increasing agent, texture improving agent, stabilising agent.

The method of the invention can in principle be performed with all proteins that are susceptible to crosslinking by an appropriate enzyme. Examples of proteins that can be dried according to the invention comprise milk proteins, such as casein and caseinates and enzymatic derivatives thereof, whey proteins, in particular α-lactalbumin, β-lactoglobulin and other animal proteins, such as egg white and blood or plasma proteins, vegetable proteins, such as soy proteins, rice proteins, potato proteins, and cereal proteins, such as wheat proteins, including gluten, glutenin, gliadin and soluble or deamidated fractions thereof, corn proteins, including zein and soluble fractions thereof, barley proteins, including hordeins and soluble fractions thereof. It was found that the method is particularly suitable for drying caseinate.

In order to control the drying process, the solution containing the crosslinked protein can be heated to adjust the viscosity temporarily, as is normally done in drying operations. Preferably this heating is to about 120° C. after which the solution is applied directly to the rollers heated to approximately the same temperature.

The term "crosslinked protein(s)" as used in this application is intended to mean "at least two protein molecules having at least one covalent bond between them".

The present invention will be further illustrated in the examples that follow and which are in no way intended to limit the invention.

BRIEF DESCRIPTION OF THE DRAWINGS

In the examples reference is made to the following figures.

DETAILED DESCRIPTION OF THE PREFERRED EMBODIMENTS

EXAMPLES

Example 1

Roller Drying a Crosslinked Protein Solution

A solution of sodium caseinate (20% w/w; viscosity 300 mPa·s at 70° C.) is reacted with the enzyme transglutaminase [E.C. 2.3.2.13] using 3 units of enzyme per gram caseinate for 1 hour at a temperature of 50° C. The enzyme is deactivated by a heat treatment (90-120° C. for 30 to 2 minutes, respectively). This treatment typically results in an increase in viscosity from 0.1-0.5 Pa·s to 1-10 Pa·s at a shear rate of 100 $s^{-1}$ at 70° C. (double gap Z1 geometry). viscosity measurements show that the crosslinked caseinate solution has now shear-thinning properties.

Figure 1:
FIG. 1 is a photograph of a continuous protein film produced on a roller dryer with a crosslinked protein solution according to the invention.
Figure 2:
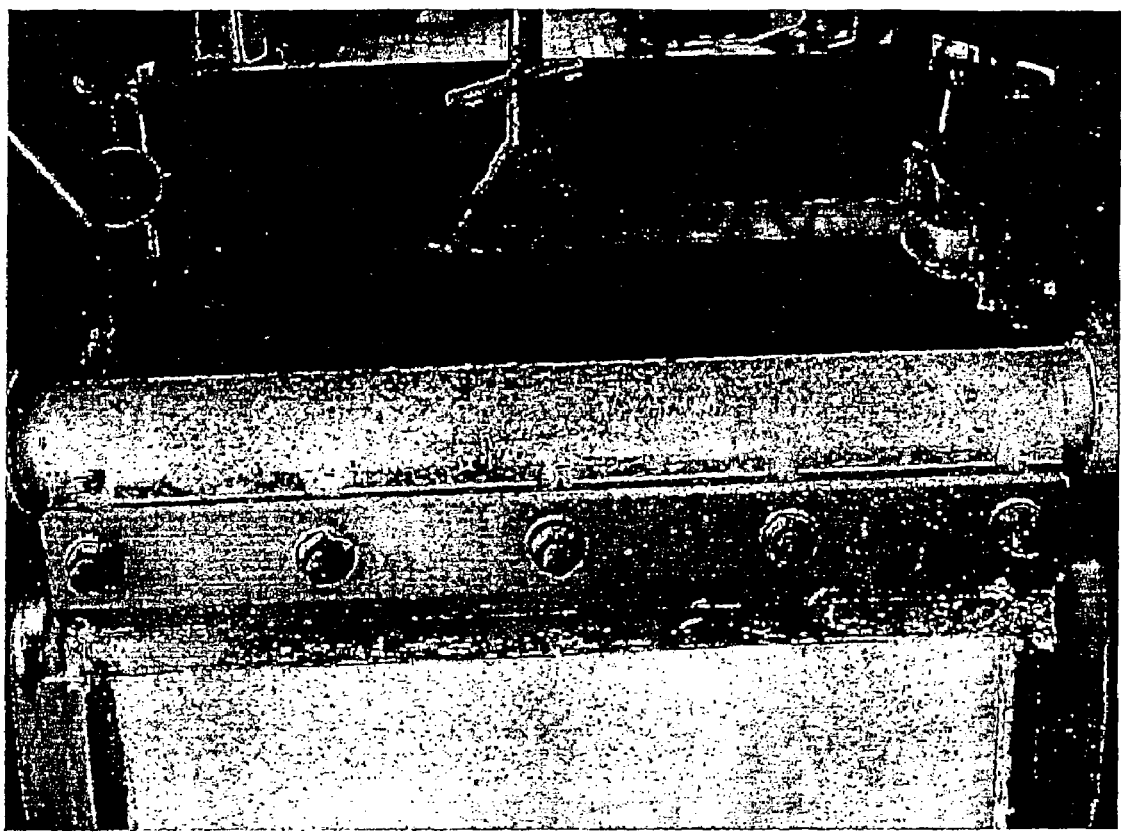
FIG. 2 is a photograph of the same roller dryer as shown in FIG. 1 in which the viscosity of the crosslinked protein preparation is visible.

The crosslinked caseinate solution that has been treated to deactivate the enzyme activity is applied directly to the roller dryer (capacity 10-30 kg per hour) operating at a steam pressure of 2-3 bar and a roller speed of 10-20 rpm. The roller drier is a pilot machine of the make "GMF", equipped as a single drum drier. The drum has a diameter of 50 cm, and a length of 50 cm. Despite it's low protein concentration, an excellent protein film was formed on the drum, which could be removed efficiently by the built-in knives (FIGS. 1 and 2). The dried film is removed by the built-in knives and fed to a milling machine and sieve.

Figure 5:
FIG. 5 is a microphoto of roller dried, crosslinked sodium caseinate.

The product thus obtained was redissolved in water to a solids content of 20% (w/w). The viscosity of the solution was measured under the conditions described above and was 8.9 Pa·s. The micrograph of FIG. 5 (Microscope: Wild M20, dispersion in xylol) shows the microscopic characteristics of a roller dried caseinate product according to the invention, displaying particles of irregular shape, which show frayed ends.

Figure 6:
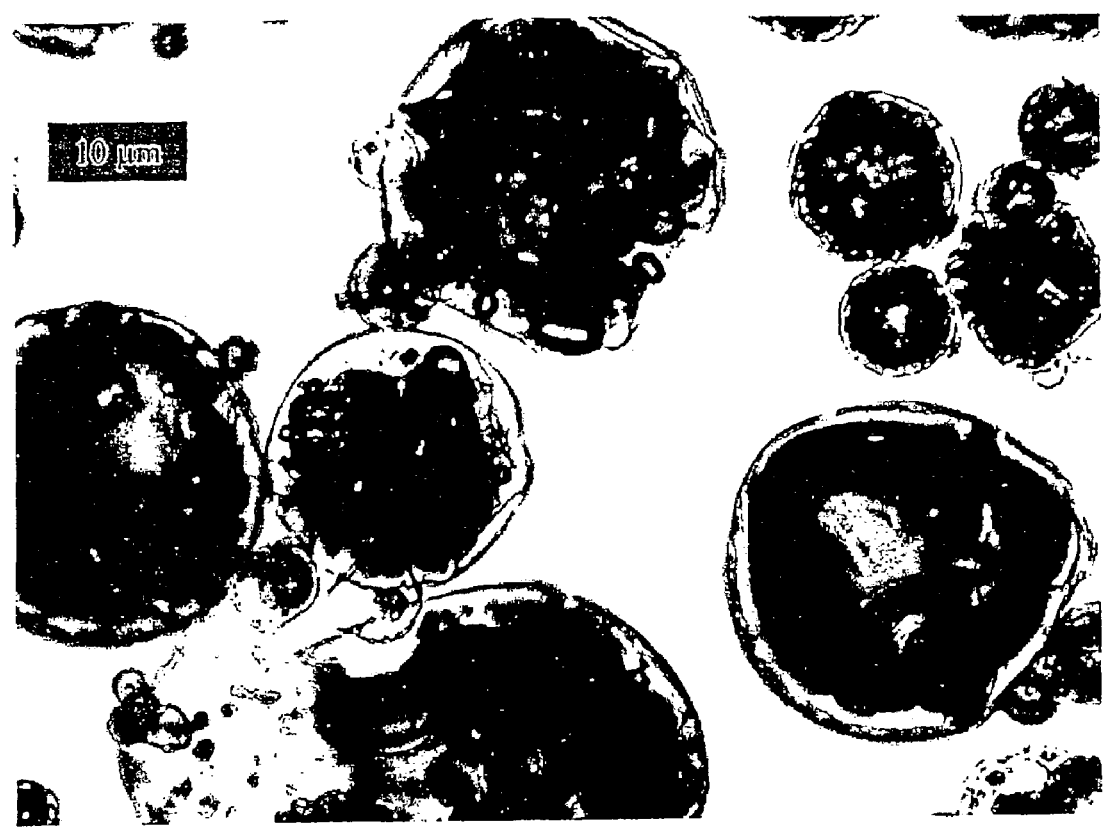
FIG. 6 is a microphoto of spray dried sodium caseinate.

FIG. 6 shows for comparison a micrograph of spray dried sodium caseinate. The particles are so-called spray globules filled with air pockets.

Example 2

Comparative Example

Figure 3:
FIG. 3 is a photograph of a discontinuous protein film produced on a roller dryer with a non-crosslinked protein solution.
Figure 4:
FIG. 4 is a photograph of the same roller dryer as shown FIG. 3 in which it is shown that the viscosity of the non-crosslinked protein preparation is insufficient to keep the solution on the roller dryer drum.

A solution of sodium caseinate (20% w/w; viscosity 300 mpa.s at 70° C., not crosslinked), is applied to the roller drier under the same conditions as in example 1. The solution appears to be too thin to apply to the drum in a good manner (FIG. 4). A part of the applied feed pours off the drum. The part of the feed solution that remains on the drum results in a very thin, irregular and discontinuous dried film, showing open patches (FIG. 3). The built in knives could merely remove thin pieces of film and dusty powder.

The invention claimed is:

1. A method for preparing a dried casein or caseinate protein powder preparation, comprising roller drying a solution of casein or caseinate proteins having a relatively low protein content of less than 40%, wherein the casein or caseinate proteins in the solution are directly crosslinked by covalent bonds by means of transglutaminase enzymatic treatment prior to roller drying the solution of casein or caseinate protein to form said dried casein or caseinate protein powder preparation.

2. The method as claimed in claim 1, wherein prior to roller drying, direct crosslinking of the casein or caseinate protein powder preparation is achieved by exposing an amount of the protein to an amount of crosslinking transglutaminase enzyme during an amount of reaction time.

3. The method as claimed in claim 2, wherein the amount of the protein is 5-30% (w/w), the amount of crosslinking transglutaminase enzyme is 0.01-20 units per gram protein and the reaction time is 0.5-12 hours.

4. The method as claimed in claim 1. wherein the protein content is 10-25%.

5. The method as claimed in claim 1, wherein the protein content is about 20%.

6. The method as claimed in claim 1, wherein the viscosity of the protein solution is in the range 1-10 Pa·s at a shear rate of 100 $s^{-1}$ at 70° C. measured at a Physica UDS200 rheometer with DIN double gap 21 geometry or a comparable device.

* * * * *